United States Patent [19]

Morand et al.

[11] Patent Number: 5,045,563
[45] Date of Patent: Sep. 3, 1991

[54] PHOTOTOXIC COMPOUNDS FOR USE AS INSECT CONTROL AGENTS

[75] Inventors: Peter Morand; John T. Arnason, both of Ottawa; Bernard J. R. Philogene, Gloucester; Anita M. MacEachern; Leonard C. Leitch, both of Ottawa; Jerzy Kaminski, Gloucester, all of Canada

[73] Assignee: Her Majesty the Queen as represented by the Minister of National Defence of Her Majesty's Canadian Government, Ottawa, Canada

[21] Appl. No.: 901,054

[22] Filed: Aug. 26, 1986

[51] Int. Cl.$^5$ ................. C07D 409/14; C07D 409/04; A01N 43/10
[52] U.S. Cl. .................................... 514/444; 546/212; 546/280; 548/527; 548/203; 549/59; 549/80; 549/60; 514/326; 514/422
[58] Field of Search ........................... 514/444; 549/59

[56] References Cited

U.S. PATENT DOCUMENTS 3,050,442  8/1962  Bijloo et al. .................... 514/444

Primary Examiner—Robert T. Bond
Attorney, Agent, or Firm—Millen, White & Zelano

[57] ABSTRACT

A method is provided herein for controlling insects which are harmful to agriculture and forestry and which are also harmful both to humans and to domestic animals. The method involves the steps of applying to a locus infested with such insects, a composition comprising a carrier and a biocidal-amount of a specifically-recited phototoxic, naturally-occurring thiophene, acetylene, or a synthetic, structurally-related derivative, analogue or acetylenic compound. Then, that composition, while at that locus, is subjected to UV radiation in the range of about 300 nm to about 400 nm, for a sufficient time to impart, to such phototoxic naturally-occurring thiophene, acetylene, or synthetic structurally-related derivative, analogue or acetylenic compound the desired insect control activity. Certain of these phototoxic naturally-occurring thiophenes, or acetylenes or synthetic, structurally-related compounds are also novel and provide novel insect control compositions.

31 Claims, No Drawings

PHOTOTOXIC COMPOUNDS FOR USE AS INSECT CONTROL AGENTS

BACKGROUND OF THE INVENTION (i) Field of the Invention

This invention relates to naturally-occurring thiophenes, acetylenes and synthetic, structurally-related derivatives, analogues or acetylenic compounds, to compositions containing such compounds, and to the use of such compositions as insect control agents with a novel phototoxic mode of action.

(ii) Description of the Prior Art

It is now well known that many hydrocarbon compounds containing non-heterocyclic groups therein have pesticidal activity and can provide pesticidal compositions. Among the patents which disclose such compounds, and that use, are the following Canadian Patents: 508,018, 675,157, 720,767, 734,397, 843,918, 869,518 and 1,028,945. However, many of such pesticides are neurotoxins, with the result that many insects develop resistance thereto.

The novel phototoxic mechanism of thiophenes and related acetylenes is a means of overcoming this resistance problem. Phototoxicity involves the absorbtion of light by the sensitizer molecule (thiophene or acetylene) and subsequent reaction of the sensitizer in its excited state causing deleterious biological effects. Discovery of the phototoxic effects of thiophenes to nematodes were first reported by F. Gommers (1972, Nematalogica 18, 458) and discovery of the phototoxic effects of polyacetylenes to microorganisms by Towers et al. (1977, Lloydia 40, 487-496).

Early work reports the toxicity of acetylenes and thiophenes to invertebrates without mention of the role of light in the process. For example, U.S. Pat. No. 3,050,442 issued Aug. 21, 1962 to J. D. Bijloo et al, provided a teaching that compositions containing

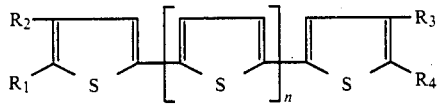

wherein n represents a number selected from the group consisting of 0 and 1, $R_1$, $R_2$, $R_3$ and $R_4$ each represents substituents selected from the group consisting of hydrogen, methyl propionyl, halogen, nitro, acetyl and phenyl radicals, with the further proviso that when n represents 0, then, $R_3$ represents, in addition, the thiophene radical and $R_2$ and $R_4$ represent only hydrogen. Within such constraints, i.e. when n=1 and $R_1=R_2=R_3=R_4=H$, the formula represents the naturally-occurring compound

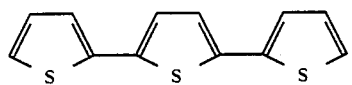

(α-terthienyl). The patentee taught that such a compound would have pesticidal effects and could be used for combatting insect pests.

It has been reported that some naturally-occurring polyacetylenes and their thiophene derivatives are toxic to invertebrates. Thus, it has been reported that cis-dehydromatricaria ester isolated from *Solidago altimissa*, and tridec-1-ene-3,5,7,9,11-pentyne isolated from *Xanthium canadense* (see S. Nakajima et al, 1977, Agric. Biol. Chem., 41, 1801-1805) both of which are widely distributed in the Asteraceae, are ovicidal to the fruit fly *Drosophila melanogaster* and the house fly, *Musca domestica*. Several polyacetylenes, e.g., α-terthienyl from *Tagetes* spp (see A. R. Verhagen et al, 1974 Arch. Dermatol, 110, 441) and two isomeric polyacetylenes from *Carthamus tinctorium* (see S. Kogiso et al, 1976 Agric. Biol. Chem. 40, 2085-2089) have been found to be nematocidal.

It has also been taught (see D. McLachlan et al, 1982, Experimentia, 38, 1061-1062) that 1-phenylhepta-1,3,5-triyne (PHT), a polyacetylenic compound isolated from *Bidens pilosa* L. (Asteraceae) has antifeedant properties towards larvae of the polyphagous insect *Eaxoa messoria*.

Recent work has demonstrated that the toxicity of polyacetylenes and thiophenes to insects is greatly enhanced by sources of radiation in the range 300-400 nm. Nine of 14 substances tested were phototoxic to mosquito larvae of *Aedes aegyptii* at 500 ppb (C. K. Wat et al, 1981, Biochem. Syst. & Ecol. 9, 59-63), yet had no effect at this concentration in the dark. The exceptional phototoxicity of two compounds, α-terthienyl and 2-(non-trans en-3',5',7'-triynyl) furan were subsequently reported (J. T. Arnason et al, 1981, Biochem. Syst. & Ecol. 9, 63-69). Analogues and derivatives of these compounds were also found to be toxic to mosquito larvae (J. T. Arnason et al, 1986, Phytochem., in press and J. Kagan et al. 1983 Insect Sci. App. 4, 377-381). Large scale synthesis of α-terthienyl permitted field trials in natural breeding pools of mosquito larvae that have demonstrated that good control can be achieved at applications of 100 g active ingredient/ha. with acceptable non target effects. (Philogène et al. 1985, J. Econ. Ent. 78, 121 and 1986, J. Chem. Ecol. in press).

With insects other than mosquito larvae, there are reports of the phototoxicity of α-terthienyl to larvae of *Manduca sexta* (K. Downum et al, 1984, Pest. Biochem. Physiol. 22, 104) and to larvae of *Euxoa messoria* (D. Champagne et al, 1984 Experientia, 40, 577. J. Kagan et al, 1983, Experimentia, 39, 402-403) reported photoovicidal activity several substances to *Drosophila melanaogaster*.

D. E. Champagne et al. in Journal of Chemical Ecology Vol. 12 No. 4, 1986 p 835, discloses the effect of the following seven structures on three species of herbivorous insects: a monothiophene, a bithiophene, α-terthienyl, phenylheptatriyne, phenylheptadiynene, phenylheptadiynene acetate and matricaria lactone. It was taught that the biosynthetically derived thiophenes were more toxic than their acetylene precursors and that toxicity increased with increasing number of thiophene rings for this series.

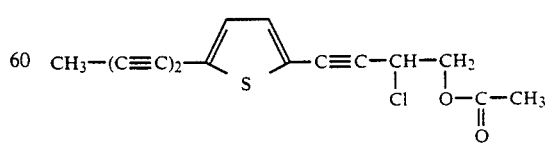

I

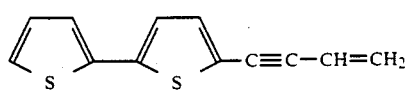

II

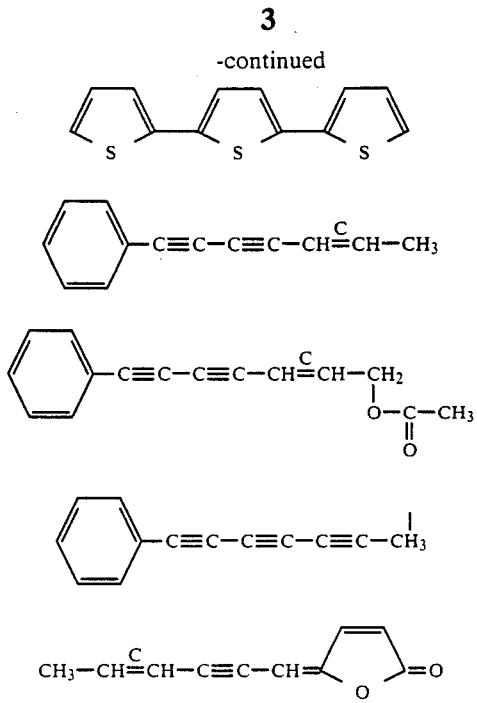

III

IV

V

VI

VII

Towers et al, in Canadian Patent No. 1,173,743 patented Sept. 4, 1984, provided a method for protecting plants from herbivores and pathogens, by applying, to the plants, a composition comprising an inert carrier and a biocidal-amount of a conjugated polyacetylene; and subjecting the composition, when on those plants, to UV radiation in the range of 300 nm to 400 nm. That patent also provided a pesticidal composition comprising an inert carrier and an amount of a conjugated polyacetylene which, when applied at a rate of 0.1 lb/acre to a plant, and then subjected to UV radiation in the range of 300 nm to 400 nm, had pesticidal activity. The conjugated polyacetylenes taught therein could be one or more of the following:
1-phenylhepta-1,3,5-triyne,
[5-(but-3-en-1-ynyl)]5'-methyl$\alpha$-bithiaine methyl-4-methythiodeca-2,4-dien-6,8-diyn-1-oate,
methyldodeca-cis.-2,8,10-trien-4,6-diyn-1-oate,
($2^1$-phenylethyl)-undeca-2,4-dien-8,10-diyn-1-carboxamide,
dodec-1-en-3,5,7,9,11-pentayne,
2-(but-3'-yn-2'-onylidenyl)-5-pentyl-tetrahydropyran,
3-[prop-1-yne]-6-(hexa-3'3'-dien-1-ynyl)-1,2-dithianine,
2-(3'-buten-1-ynyl)-5-(3'-penten-1-ynyl)-thiophene,
$\gamma$-(2'-neuynylidenyl)-$\gamma$-but-2-enyrolactone,
1-acetoxytetradeca-4,6,12-trien-8,10-diyne,
tetradeca-4,6-dien-8,10,12-triynyl-sec-butenoate,
1,2-dihydroxytrideca-3,5-dien-7,9,11-triyne,
2-(non-trans-1'-en-3',5',7'-triynyl)-tetrahydropyran,
2-(non-trans-en-3',5'7'-triynyl)-furan,
heptadeca-1,9,6-trien-4,6-dien-3-one,
1,3-dihydroxytetradeca-4,6,12-trien-8,10-diyne,
1-hydroxy-7-phenylhepta-2-en-4,6-diyne,
2-chloro-1-hydroxytrideca-3,11-dien-5,7,9-triyne,
7-phenylhepta-2-en-4,6-diynal,
$\gamma$-(hex-4'-en-2'-ynylidenyl)-$\gamma$-but-2-enyrolactone,
heptadeca-1,8,15-trien-11,13-diyne,
nonadeca-1,7,9,17-tetraen-11,13-diyne,
3,4-dihydroxytrideca-1,5,11-trien-7,9-diyne,
trideca-1,3,5,11-tetraen-7,9-diyne,
1,2-dihydroxytrideca-3,11-dien-5,7,9-triyne,
1-hydroxytetradeca-6,8,11,13-tetraen-10-yne,
1-acetoxytetradeca-6,8,12,14-tetraen-10-yne,
1,3-dihydroxytetradeca-trans, trans-4,6-dien-8,10,12-triyne,
1,3-diacetoxytetradeca-4,6-dien-8,10,12-triyne,
tetradeca-1,8,13-trien-4,6-diyn-3-one,
1-hydroxy-7-phenylhepta-2,4,6-triyne,
7-phenylhepta-2,4,6-triynal;
5-acetoxy-7-(penta-2',4'-diynylidenyl)-2,6-dioxa-(4,4-spiro-nona-3,8-diene);
1-[5'-pentyl-3',4',5',6'-tetrahydrophyranilidenyl]but-3-yne-2-one; and
(3-hydroxy-2-[trans-1'-nonen-3,5,7-trynyl]-tetrahydropyran.

Other compounds which are structurally related to the above discussed compounds which have been disclosed in the scientific literature are these listed in the following Table 1.

TABLE 1

| COMPOUND (FORMULA) | COMPOUND NO. | DISCLOSED IN REFERENCE NO. |
|---|---|---|
| The following fourteen compounds of Formula I: | | |
| FORMULA I | 1. $R^1 = R^2 = Br$ | #2, #3 and #5 |
| | 2. $R^1 = R^2 = CH_3$ | #3, #12, #13 |
| | 3. $R^1 = R^2 = CO_2H$ | #6 |
| | 4. $R^1 = R^2 = CO_2CH_3$ | #6 |
| | 5. $R^1 = R^2 = C(CH_3)_3$ | #11 |
| | 6. $R^1 = CH_3; R^2 = H$ | #3 |
| | 7. $R^1 = CO_2H; R^2 = H$ | #6 |
| | 8. $R^1 = CO_2CH_3; R^2 = H$ | #6 |
| | 9. $R^1 = $ tritium; $R^2 = COCH_3$ | #8 |
| | 10. $R^1 = R^2 = COCH_3$ | #8, #9 |
| | 11. $R^1 = R^2 = C_6H_5$ | #10 |
| | 12. $R^1 = CH_2OH; R^2 = H$ | #11 |
| | 13. $R^1 = Br; R^2 = H$ | #12 and #13 |
| | 14. $R^1 = CHO; R^2 = H$ | #6 |
| FORMULA II | 15. | #1 and #4 |
| FORMULA III | | |

TABLE 1-continued

| COMPOUND (FORMULA) | COMPOUND NO. | DISCLOSED IN REFERENCE NO. |
|---|---|---|
| 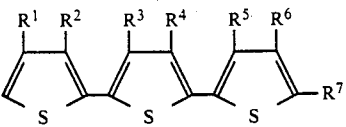<br>FORMULA IV | 16. $R^1 = R^2 = R^3 = R^4 = R^5 = R^6 = CH_3$; $R^7 = H$<br>17. $R^1 = R^2 = R^5 = R^6 = R^7 = H$; $R^3 = R^4 = CH_3$<br>18. $R^1 = R^2 = R^5 = R^6 = R^7 = CH_3$; $R^3 = R^4 = H$<br>19. $R^1 = R^4 = R^6 = R^7 = H$; $R^2 = R^3 = R^5 = CH_3$ | #5<br>#5a and 5b<br>#5<br>#5 |
| 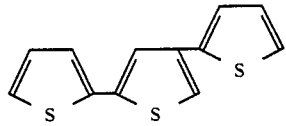<br>FORMULA V | 20. | #5 and #7 |
| 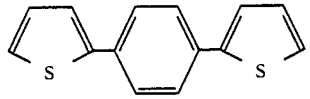<br>FORMULA VI | 21. $R^1 = R^2 = R^3 = R^4 =$ tritium | #8 |
| 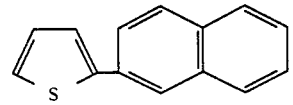<br>FORMULA VII | 22. | #5a |
| 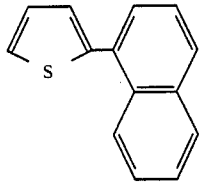<br>FORMULA VIII | 23. | #14 |
| 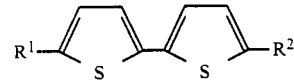<br>FORMULA IX | 24. | #7 |

The following two compounds of Formula IX:

| | | |
|---|---|---|
| 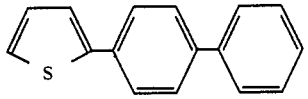<br>FORMULA X | 25. $R^1 = H$; $R^2 = Br$<br>26. $R^1 = R^2 = .Br$ | 15<br>#15 |
| 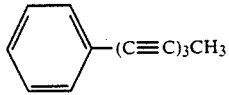<br>FORMULA XI | 27. | #16 |
| 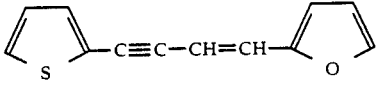<br>FORMULA XII | 28. | #17 and #18 |
| C≡C—CH=CH<br>FORMULA XIV | 29. | #19 |

TABLE 1-continued

| COMPOUND (FORMULA) | COMPOUND NO. | DISCLOSED IN REFERENCE NO. |
|---|---|---|
| FORMULA XV (structure shown) | 30. | #20 |
| FORMULA XVI (structure shown) | 31. | #24 and #25 |
| FORMULA XVII (structure shown) | 32. | #21, #22 and #23 |
| FORMULA XVIII: $CH_3-(C\equiv C)_3-CH=CH-\text{(furan)}$ with Z | 33. | #18 |
| 34: $CH_3-(C=C)_3-CH=CH-CH\underset{O}{\overset{}{\diagdown\diagup}}CH-CH=CH_2$ with Z | 34. | #26 |

In the above table, the references identified as numbers 1-28 are as follows:

1 = K. Tamao et. al., Tetrahedron, Vol. 38 #22, 3347-3354, (1982).
2 = References given in B. J. R. Philogène, et. al., Journal of Economic Entomology, Vol 78 #1 pp 121-126, (1985).
3 = J. W. Sease and L. Zechmeister, J. Am. Chem. Soc 69, 270, (1947).
4 = A. Meuller et. al., Acta Chem Acad Sci Hung, 52, 261 (1961) Chem Abstr, 67, 64222 (1967).
5a = J. H. Uhlenbroek and J. D. Bijloo, Rec Trav Chim, 79, 1181-96, (1960) Eng.
5b = H. J. Bestmann and W. Schaper, Tetrahed. Letters, No 3, pp 243-244 (1979).
6 = J. Kagan, et. al., J. Org. Chem., 48, 4076-4078, (1983).
7 = H. Wynberg et. al., J. Am. Chem. Soc. 79, 1972 (1957).
8 = F. Bohlmann et. al., Chem. Ber. 99, (3), 984, (1966).
9 = H. Wynberg et. al., J. Am. Chem. Soc., 82, 1447, (1960).
10 = K. E. Schulte et. al., Arch. Pharm. 296, 456, (1963).
11 = M. Sy et. al., J. Chem. Soc., 1975, (1954).
12 = CA 55: P 1800 2d.
13 = CA 58: P4991a.
14 = H. Wynberg et. al., J. Am. Chem. Soc., 89, #14, 3487-94. (1967).
15 = A. Carpita, R. Rossi, and C. Veracini, Tetrahedron Vol. 41, #1, pp 1919-1929, (1985).
16 = P. Riberreau, G. Quequiner and P. Pastour, Bull. Soc. Chim. Fr., 4, pp 1581-7, (1972).
17 = J. Meier, W. Chodkiewicz, P. Cadiot, and A. Willemart, Compt. Rend. 245, 1634, (1957).
18 = Patented by T. Arnason et al.. Canadian Patent No. 1,169,767, and Canadian Patent No. 1,173,743.
19 = Commercially Available
20 = P. Chauvin, J. Morel, P., Pastour and J. Martinez. Bull. Soc. Chim. Fr. (9-10 Pt 2) pp 2079-85, (1974).
21 = P. Raymond, Compt. Rend. 202, pp 854-6, (1936)
22 = E. Campaigne, and L. Fedor, Journal of Heterocyclic Chem. 1 (5), pp 242-4, (1964).
23 = R. E. Atkinson, R. F. Curtis and J. A. Taylor, J. Chem. Soc (C) 7, pp 578-82, (1967).
24 = R. E. Atkinson, R. F. Curtis And G. J. Philips, Chem. Ind, 51, pp 2101-2102, (1964).
25 = CA 96: P117583r; CA 96 P16085z.
26 = F. Bohlmann et al, Tett. Lett, (19) pp 1385-8, (1965).

Nevertheless, it is well established that the biological activity of naturally-occurring thiophenes and acetylenes and synthetic, structurally-related derivatives, analogues or acetylenic compounds is not predictable. Moreover, such naturally-occurring thiophenes, acetylenes and synthetic, structurally-related derivatives, analogues or acetylenic compounds, to be biologically useful, should also be relatively stable but should leave no toxic residue, and such characteristics are also not predictable. Accordingly, it is an object of this invention to provide novel phototoxic, naturally-occurring thiophenes, acetylenes, or synthetic, structurally-related derivatives, analogues or acetylenic compounds which have a selected balance between stability and biodegradability and consequently have improved utility as insect control agents.

It would also be desirable, and it is also an object of this invention, to provide pesticidal compositions containing phototoxic, naturally-occurring thiophenes, acetylenes, or synthetic, structurally-related derivatives, analogues or acetylenic compounds, in which such phototoxic, naturally-occurring thiophenes, acetylenes or synthetic, structurally-related derivatives, analogues or acetylenic compounds are relatively stable but which are eventually biodegradable and would therefore leave no long-lived toxic residues.

It would also be desirable, and it is therefore yet another object of this invention to provide methods for insect control involving the use of phototoxic, naturally-occurring thiophenes, acetylenes, or synthetic, structurally-related derivatives, analogues or acetylenic compounds which are relatively stable but which are eventually biodegradable and generally would leave no long-lived toxic residues.

(ii) Statements of Invention

This invention now provides a method for controlling insects which are harmful to agriculture, and forestry and are harmful with respect to veterinary and human medicine, which method comprises: (a) applying to a locus infested with such insects, a composition comprising a carrier and a biocidal-amount of a phototoxic naturally-occurring thiophene, acetylene or synthetic, structurally-related derivatives, analogues or acetylenic compounds selected from the group consisting of the following numbered compounds identified as numbers 1 through 70:

(a) the fourteen compounds, 1–14, of Formula I:

FOMULA I

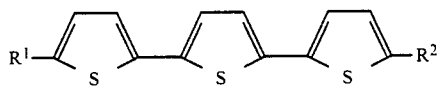

(1) $R^1 = R^2 = Br$;

(2) $R^1 = R^2 = CH_3$;

(3) $R^1 = R^2 = CO_2H$;

(4) $R^1 = R^2 = CO_2CH_3$;

(5) $R^1 = R^2 = C(CH_3)_3$;

(6) $R^1 = CH_3$; $R^2 = H$;

(7) $R^1 = CO_2H$; $R_2 = H$;

(8) $R^1 = CO_2CH_3$; $R^2 = H$;

(9) $R^1 = $ tritium; $R^2 = COCH_3$;

(10) $R^1 = R^2 = COCH_3$;

(11) $R^1 = R^2 = C_6H_5$;

(12) $R^1 = CH_2OH$; $R^2 = H$;

(13) $R^1 = Br$; $R^2 = H$;

(14) $R^1 = CHO$; $R^2 = H$;

(b) the compound, 15, of Formula II:

FORMULA II

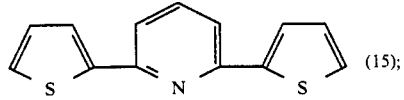

(c) the four compounds, 16–19, of Formula III:

FORMULA III

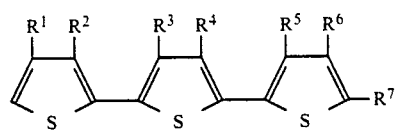

16. $R^1 = R^2 = R^3 = R^4 = R^5 = R^6 = CH_3$; $R^7 = H$

17. $R^1 = R^2 = R^5 = R^6 = R^7 = H$; $R^3 = R^4 = CH$

18. $R^1 = R^2 = R^5 = R^6 = R^7 = CH_3$; $R^3 = R^4 = H$

19. $R^1 = R^4 = R^6 = R^7 = H$; $R^2 = R^3 = R^5 = CH_3$ (d) the compound, 20, of Formula IV:

FORMULA IV

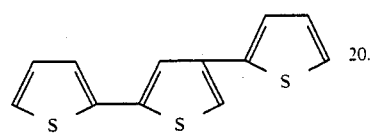

(e) the compound, 21, of Formula V:

FORMULA V

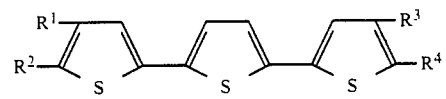

21. $R^1 = R^2 = R^3 = R^4 = $ tritium (f) the compound, 22 of Formula VI:

FORMULA VI

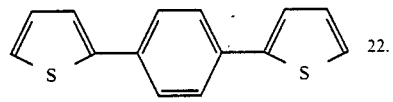

(g) the compound, 23, of Formula VII:

FORMULA VII

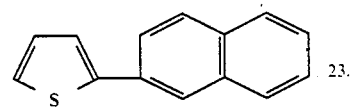

(h) the compound, 24, of Formula VIII:

FORMULA VIII

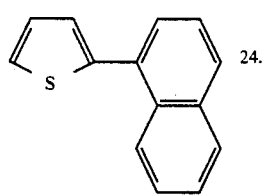

(i) the two compounds, 25 and 26, of Formula IX:

FORMULA IX

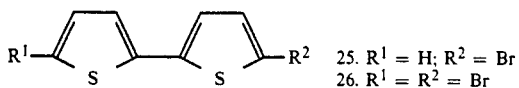
25. $R^1 = H; R^2 = Br$
26. $R^1 = R^2 = Br$ (j) the compound, 27, of Formula X:

FORMULA X

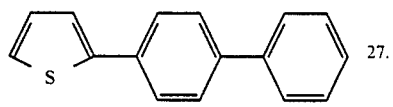

(k) the compound, 28, of Formula XI:

FORMULA XI

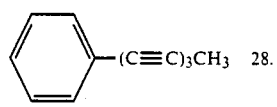

(l) the compound, 29, of Formula XII:

FORMULA XII

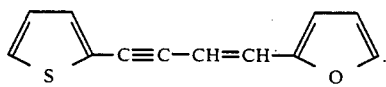

(m) the compound, 30, of Formula XIV:

FORMULA XIV

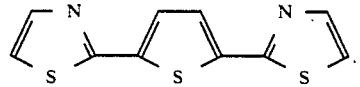

(n) the compound, 31, of Formula XV:

FORMULA XV

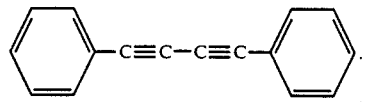

(o) the compound, 32, of Formula XVI:

FORMULA XVI

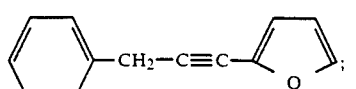
(32)

(p) the compound, 33, of Formula XVII:

FORMULA XVII (33)

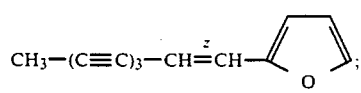

(q) the compound, 34, of Formula XVIII:

FORMULA XVIII (34)

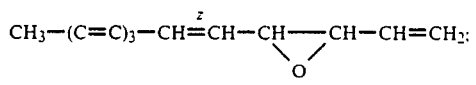

(r) a novel derivative, 35-47 of the Formula XIX:

FORMULA XIX

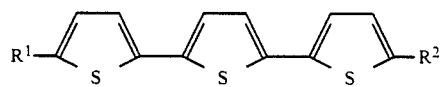

$R^1 = R^2 = I$; (35)
$R^1 = R^2 = CHO$; (36)
$R^1 = R^2 = C \equiv N$; (37)
$R^1 = R^2 = NO_2$; (38)
$R^1 = NH_2; R^2 = H$; (39)
$R^1 = C(CH_3)_3; R^2 = H$; (40)
$R^1 = (CH_2)_2OH; R^2 = H$; (41)
$R^1 = I; R^2 = H$; (42)
$R^1 = CO_2CH_2CH_3; R^1 = H$; (43)
$R^1 = C \equiv N; R^2 = H$; (44)
$R^1 = NO_2; R^2 = H$; (45)
$R^1 = CH = CHCO_2H(cis), R^2 = H$; and (46)
$R^1 = CH = CHCO_2H(trans), R^2 = H$; (47)

(s) a novel derivative, 48, of the Formula XX:

FORMULA XX

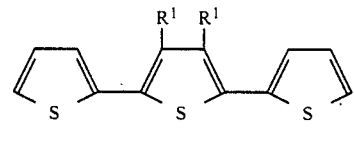

$R^1 = CH_3CH_2$;

(t) a novel analogue or a novel acetylene compound, 49-52 of the following Formulae, namely:

Formula XXI (49)

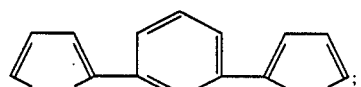

Formula XXII (50)

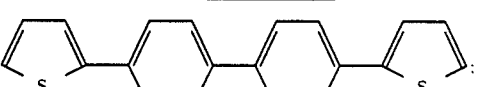

Formula XXIII (51)

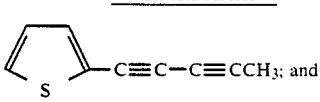

Formula XXIV

-continued

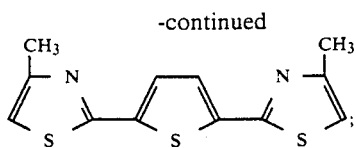
(52)

and (u) a novel derivative 53–70 of α-terthienyl of Formula XXV (where a dot indicates the point of attachment):

Formula XXV.
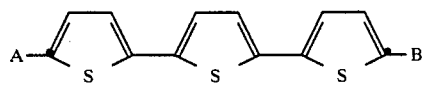

A = H, B = , and R = Cl; (53)

A = H, B = , and R = CH₃; (54)

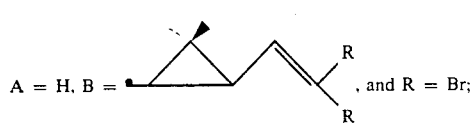
A = H, B = , and R = Br; (55)

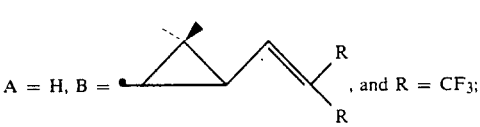
A = H, B = , and R = CF₃; (56)

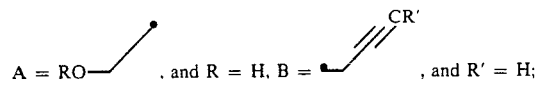
A = RO—, and R = H, B = , and R' = H; (57)

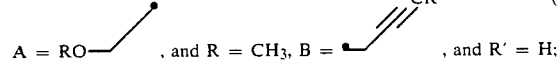
A = RO—, and R = CH₃, B = , and R' = H; (58)

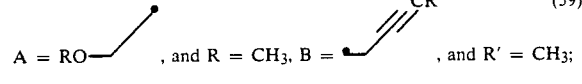
A = RO—, and R = CH₃, B = , and R' = CH₃; (59)

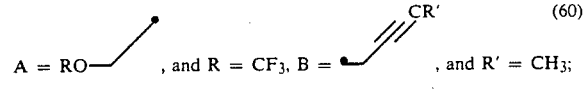
A = RO—, and R = CF₃, B = , and R' = CH₃; (60)

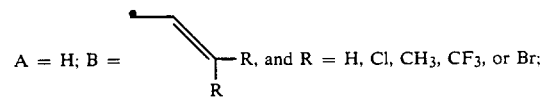
A = H; B = , R, and R = H, Cl, CH₃, CF₃, or Br; (61)

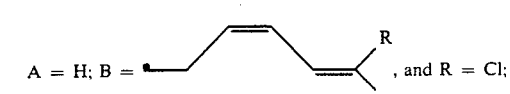
A = H; B = , and R = Cl; (62)

A = H; B = , and R = CH₃; (63)

-continued
Formula XXV

A = H; B = , and R = Br; (64)

A = H; B = , and R = CF₃; (65)

A = H, B = —OCH₃; (66)

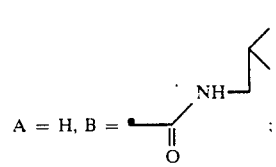
A = H, B = ; (67)

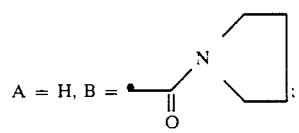
A = H, B = ; (68)

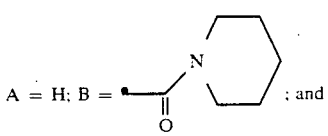
A = H; B = ; and (69)

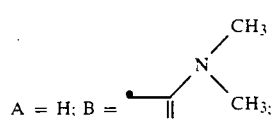
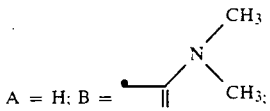
A = H; B = ; (70)

and (b) subjecting that composition at that locus to UV radiation in the range of about 300 nm to about 400 nm for a sufficient time to impart, to such phototoxic naturally-occurring thiophene, acetylene or synthetic, structurally-related derivative, analogue or acetylenic compound such insect controlling activity.

This invention also provides an insect control composition comprising a carrier and a biocidally-effective amount of a phototoxic, naturally-occurring thiophene, acetylene, or synthetic, structurally-related derivative, analogue or acetylenic compound selected from the group consisting of the following compounds identified as numbers 1 through 70:

(a) the fourteen compounds, 1–14, of Formula I:

FORMULA I
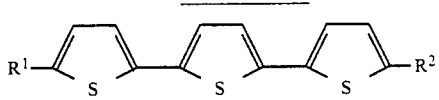

| | |
|---|---|
| $R^1 = R^2 = Br$ | 1. |
| $R^1 = R^2 = CH_3$ | 2. |
| $R^1 = R^2 = CO_2H$ | 3. |
| $R^1 = R^2 = CO_2CH_3$ | 4. |
| $R^1 = R^2 = C(CH_3)_3$ | 5. |
| $R^1 = CH_3; R^2 = H$ | 6. |
| $R^1 = CO_2H; R_2 = H$ | 7. |
| $R^1 = CO_2CH_3; R^2 = H$ | 8. |
| $R^1 = $ tritium; $R^2 = COCH_3$ | 9. |

-continued
FORMULA I
$R^1 = R^2 = COCH_3$    10.
$R^1 = R^2 = C_6H_5$    11.
$R^1 = CH_2OH; R^2 = H$    12.
$R^1 = Br; R^2 = H$    13.
$R^1 = CHO; R^2 = H$    14.

(b) the compound, 15, of Formula II:

FORMULA II

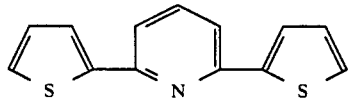

15.

(c) the four compounds, 16-19, of Formula III:

FORMULA III

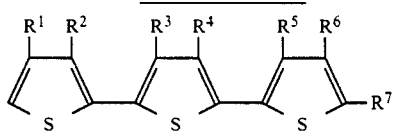

$R^1 = R^2 = R^3 = R^4 = R^5 = R^6 = CH_3; R^7 = H$   16.
$R^1 = R^2 = R^5 = R^6 = R^7 = H; R^3 = R^4 = CH$   17.
$R^1 = R^2 = R^5 = R^6 = R^7 = CH_3; R^3 = R^4 = H$   18.
$R^1 = R^4 = R^6 = R^7 = H; R^2 = R^3 = R^5 = CH_3$   19.

(d) the compound, 20, of Formula IV:

FORMULA IV

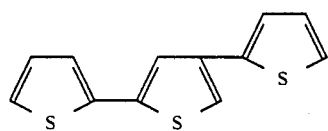

20.

(e) the compound, 21, of Formula V:

FORMULA V

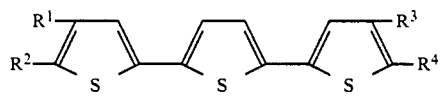

$R^1 = R^2 = R^3 = R^4 = $ tritium

21.

(f) the compound, 22 of Formula VI:

FORMULA VI

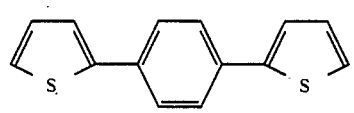

22.

(g) the compound, 23, of Formula VII:

FORMULA VII

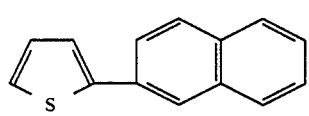

23.

(h) the compound, 24, of Formula VIII:

FORMULA VIII

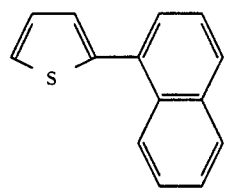

24.

(i) the two compounds, 25 and 26, of Formula IX:

FORMULA IX

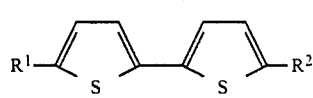

25. $R^1 = H; R^2 = Br$
26. $R^1 = R^2 = Br$ (j) the compound, 27, of Formula X:

FORMULA X

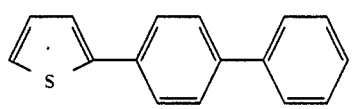

27.

(k) the compound, 28, of Formula XI:

FORMULA XI

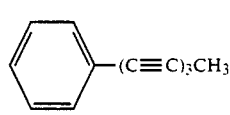

28.

(l) the compound, 29, of Formula XII:

FORMULA XII

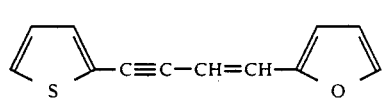

29.

(m) the compound, 30, of Formula XIV:

FORMULA XIV

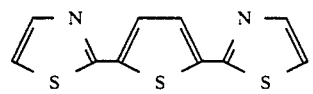

30.

(n) the compound, 31, of Formula XV:

FORMULA XV

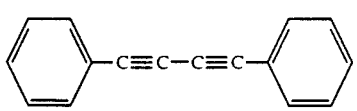

31.

(o) the compound, 32, of Formula XVI:

FORMULA XVI

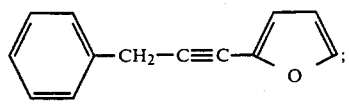

(p) the compound, 33, of Formula XVII:

FORMULA XVII

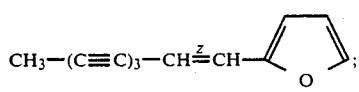 (33)

(q) the compound, 34, of Formula XVIII:

FORMULA XVIII

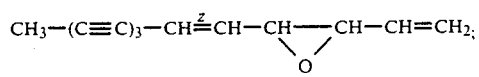 (34)

(r) a novel derivative, 35-47, of the Formula XIX:

FORMULA XIX

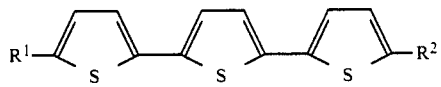

| | |
|---|---|
| $R^1 = R^2 = I$; | (35) |
| $R^1 = R^2 = CHO$; | (36) |
| $R^1 = R^2 = C \equiv N$; | (37) |
| $R^1 = R^2 = NO_2$; | (38) |
| $R^1 = NH_2$; $R^2 = H$; | (39) |
| $R^1 = C(CH_3)_3$; $R^2 = H$; | (40) |
| $R^1 = (CH_2)_2OH$; $R^2 = H$; | (41) |
| $R^1 = I$; $R^2 = H$; | (42) |
| $R^1 = CO_2CH_2CH_3$; $R^1 = H$; | (43) |
| $R^1 = C \equiv N$; $R^2 = H$; | (44) |
| $R^1 = NO_2$; $R^2 = H$; | (45) |
| $R^1 = CH = CHCO_2H(cis)$, $R^2 = H$; and | (46) |
| $R^1 = CH = CHCO_2H(trans)$, $R^2 = H$; | (47) |

(s) a novel derivative, 48, of the Formula XX:

FORMULA XX

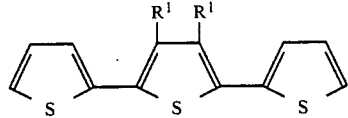

$R^1 = CH_3CH_2$; (48)

(t) a novel analogue or a novel acetylene compound, 49-52 of the following Formulae, namely:

Formula XXI

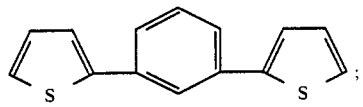 (49)

Formula XXII

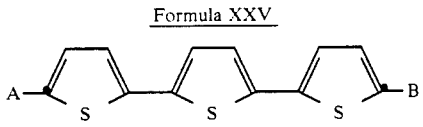 (50)

Formula XXIII

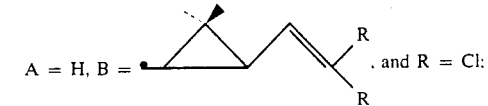 (51)

Formula XXIV

 (52)

and (u) a novel derivative 53-70 of α-terthienyl of Formula XXV (where a dot indicates the point of attachment):

Formula XXV

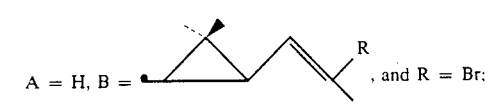

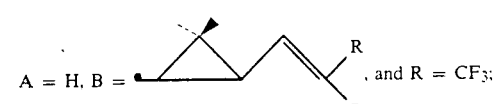 (53)

A = H, B = , and R = Cl;

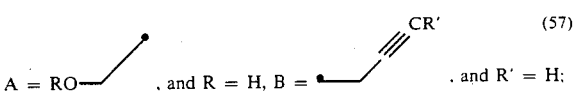 (54)

A = H, B = , and R = $CH_3$;

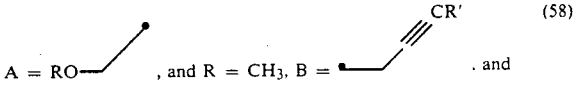 (55)

A = H, B = , and R = Br;

 (56)

A = H, B = , and R = $CF_3$;

 (57)

A = RO—, and R = H, B = , and R' = H;

(58)

A = RO—, and R = $CH_3$, B = , and

R' = H;

(59)

A = RO—, and R = $CH_3$, B = , and

R' = $CH_3$;

(60)

A = RO—, and R = $CF_3$, B = , and

-continued

R' = CH₃:

(61) 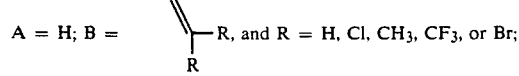
A = H; B = [structure], and R = H, Cl, CH₃, CF₃, or Br;

(62) 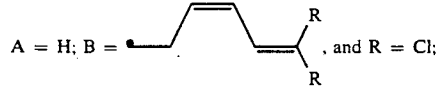
A = H; B = [structure], and R = Cl;

(63) 
A = H, B = [structure], and R = CH₃;

(64) 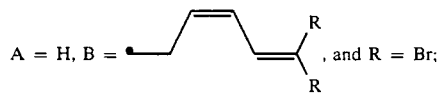
A = H, B = [structure], and R = Br;

(65) 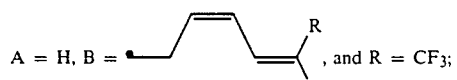
A = H, B = [structure], and R = CF₃;

(66) 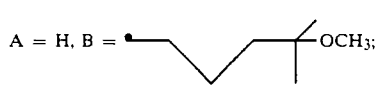
A = H, B = [structure]—OCH₃;

(67) 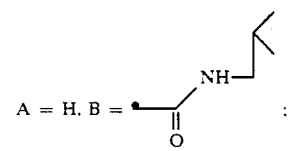
A = H, B = [structure];

(68) 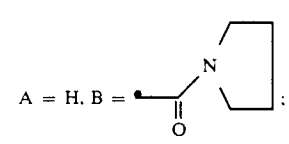
A = H, B = [structure];

(69) 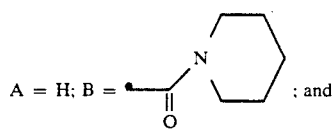
A = H; B = [structure]; and

(70) 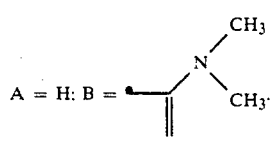
A = H; B = [structure].

This invention also provides an insect control composition comprising a carrier and a biocidally-effective amount of a phototoxic, naturally-occurring thiophene, acetylene, or synthetic, structurally-related derivative, analogue or acetylenic compound selected from the group consisting of the following compounds identified as numbers 35 through 70:

FORMULA XIX

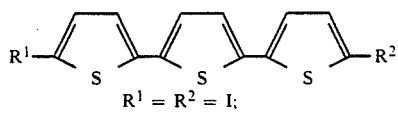

| | |
|---|---|
| $R^1 = R^2 = I$; | 35) |
| $R^1 = R^2 = CHO$; | 36) |
| $R^1 = R^2 = C\equiv N$; | 37) |
| $R^1 = R^2 = NO_2$; | 38) |
| $R^1 = NH_2; R^2 = H$; | 39) |
| $R^1 = C(CH_3)_3; R^2 = H$; | 40) |
| $R^1 = (CH_2)_2OH; R^2 = H$; | 41) |
| $R^1 = I; R^2 = H$; | 42) |
| $R^1 = CO_2CH_2CH_3; R^1 = H$; | 43) |
| $R^1 = C\equiv N; R^2 = H$; | 44) |
| $R^1 = NO_2; R^2 = H$; | 45) |
| $R^1 = CH=CHCO_2H(cis), R^2 = H$; and | 46) |
| $R^1 = CH=CHCO_2H(trans), R^2 = H$; | 47) |

(s) a novel derivative, 48, of the Formula XX:

FORMULA XX

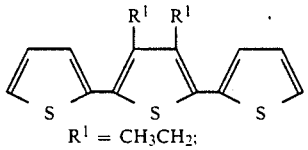

$R^1 = CH_3CH_2$; 48)

(t) a novel analogue or a novel acetylene compound, 49–52 of the following Formulae, namely, Formula XXI 49)

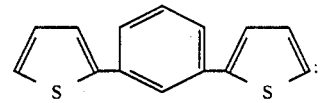

Formula XXII 50)

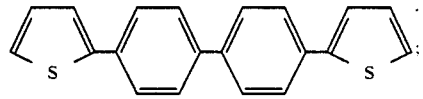

Formula XXIII 51)

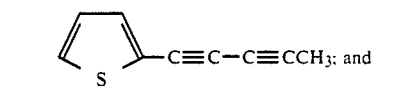

Formula XXIV 52)

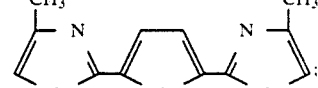

and (u) a novel derivative 53-70 of α-terthienyl of Formula XXV (where a dot indicates the point of attachment):

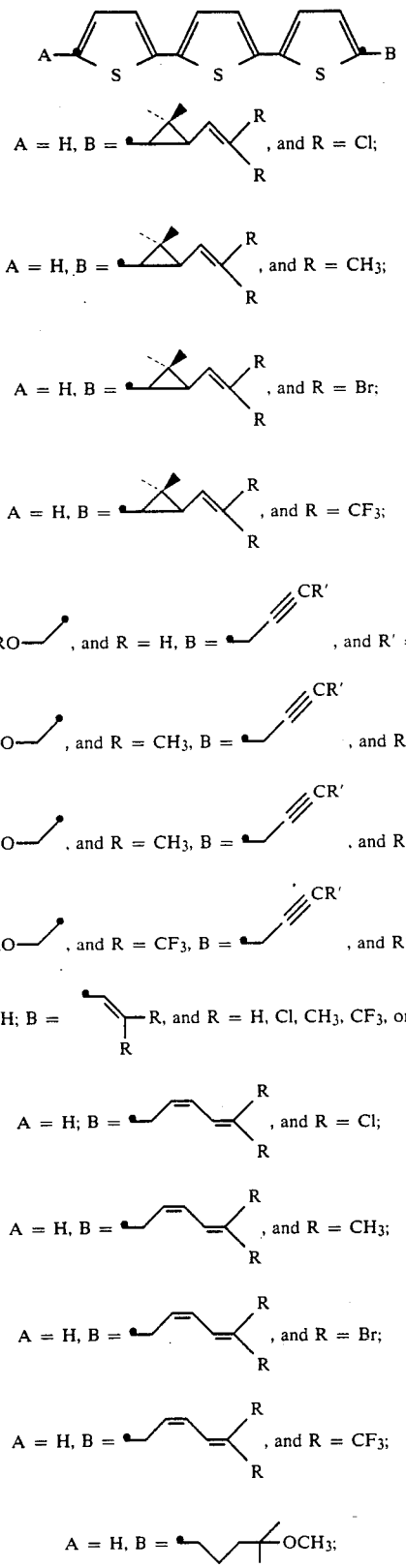

Formula XXV

53) A = H, B = [structure], and R = Cl;

54) A = H, B = [structure], and R = CH₃;

55) A = H, B = [structure], and R = Br;

56) A = H, B = [structure], and R = CF₃;

57) A = RO—[structure], and R = H, B = [structure], and R' = H;

58) A = RO—[structure], and R = CH₃, B = [structure], and R' = H;

59) A = RO—[structure], and R = CH₃, B = [structure], and R' = CH₃;

60) A = RO—[structure], and R = CF₃, B = [structure], and R' = CH₃;

61) A = H; B = [structure]—R, and R = H, Cl, CH₃, CF₃, or Br;

62) A = H; B = [structure], and R = Cl;

63) A = H, B = [structure], and R = CH₃;

64) A = H, B = [structure], and R = Br;

65) A = H, B = [structure], and R = CF₃;

66) A = H, B = [structure]—OCH₃;

-continued
Formula XXV

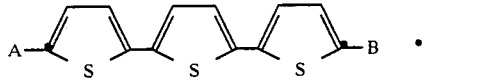

67) A = H, B = 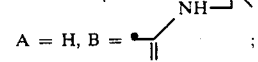;

68) A = H, B = 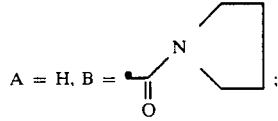;

69) A = H; B = 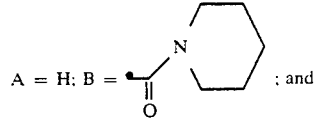; and

70) A = H; B = 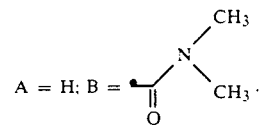.

(iii) Other Features of This Invention

In one feature of this method embodiment of this invention, the selected phototoxic, naturally-occurring thiophene, acetylene, or synthetic, structurally-related derivative, analogue or acetylenic compound is a compound selected from those identified above as numbers 1 through 34.

In accordance with another feature of this method embodiment of the present invention, the selected phototoxic, naturally-occurring thiophene, acetylene or synthetic, structurally-related derivative, analogue or acetylenic compound is a novel derivative which is selected from those identified above as numbers 35 through 48.

In accordance with yet another feature of this method embodiment of the invention, the selected phototoxic, naturally-occurring thiophene, acetylene or synthetic, structurally-related derivative, analogue or acetylenic compound is a novel analogue or acetylenic compound which is selected from those identified above as numbers 49 through 52.

In accordance with still another feature of this method embodiment of the invention, the selected phototoxic, naturally-occurring thiophene, acetylene or synthetic, structurally-related derivative, analogue or acetylenic compound is a novel analogue or acetylenic compound which is selected from those identified above as numbers 53 through 70.

In accordance with one feature of this composition embodiment of the present invention, the selected phototoxic, naturally-occurring thiophene, acetylene, or synthetic, structurally-related derivative, analogue or acetylenic compound is selected from those identified above as numbers 1 through 34.

In accordance with another embodiment of this composition embodiment of the present invention, the selected phototoxic, naturally-occurring thiophene, acetylene, or synthetic, structurally-related derivative, analogue or acetylenic compound is a novel derivative selected from those identified above as numbers 35 through 48.

In accordance with yet another embodiment of this composition embodiment of this invention, the selected phototoxic, naturally-occurring thiophene, acetylene, or synthetic structurally-related derivative, analogue or acetylenic compound is a novel analogue or acetylenic compound selected from those identified above as numbers 49 through 52.

In accordance with still another embodiment of this composition embodiment of this invention, the selected phototoxic, naturally-occurring thiophene, acetylene, or synthetic structurally-related derivative, analogue or acetylenic compound is a novel analogue or acetylenic compound selected from those identified above as numbers 53 through 70. Invention are primarily suitable for the selective control of many insects, including mosquitoes and blackflies.

The compositions of embodiments of this invention may furthermore be used by themselves or in conjunction with other well-known biodegradable pesticides. The compositions of embodiments of this invention may also include a synergistic carrier or an inert carrier. In addition, the composition may include at least one of the following additives; namely, solvents, diluents, dispersing agents and wetting agents. The compositions of embodiments of this invention may advantageously be used in the form of powders, strewable preparations, granules, solutions, emulsions and suspensions. As will be evident hereafter, these are provided by the addition of liquid and/or solid vehicles or diluents and, if desired, of surface active agents, for example, wetting, adherent, emulsifying and/or dispersing agents.

The compositions of embodiments of this invention may be provided in the form of solutions for immediate spraying using suitable organic solvents, for example, low molecular weight alcohols, hydrocarbons, e.g., alkylated naphthalene or tetrahydronaphthalene if desired with the use of xylene mixtures, cyclohexanols, ketones or chlorinated hydrocarbons, e.g., tetrachlorethane, trichloroethylene or trichlorobenzenes or tetrachlorobenzenes. Other suitable liquid carriers are, for example, water, aliphatic hydrocarbons, aromatic hydrocarbons, for example, toluene and xylene, cyclohexanone, isophorone, dimethyl sulphoxide and dimethylformamide, and also mineral oil fractions.

The compositions of embodiments of this invention may alternatively be provided in the form of aqueous mixtures using emulsion concentrates, pastes or wettable array powders and adding water thereto. Suitable emulsifying or dispersing agents are non-ionic products, for example, condensation products of ethylene oxide with aliphatic alcohols, amines or carboxylic acids containing a long-chain hydrocarbon radical with 10 to 30 carbon atoms with ethylene oxide, e.g., the condensation product from octadecyl alcohol with 25 to 30 mols of ethylene oxide, or soya bean fatty acid with 30 mols of ethylene oxide, or commercial oleylamine with 15 mols of ethylene oxide, or dodecylmercaptan with 12 mols of ethylene oxide.

Suitable anionic emulsifying agents include the sodium salt of dodecyl alcohol sulfuric acid ester, the sodium salt of dodecyl benzenesulfonic acid, the potassium or triethanolamine salt of oleic or abietic acid, of mixtures of these acids, and, the sodium salt of a petroleum-sulfonic acid.

Suitable cationic dispersing agents include quaternary ammonium compounds, e.g. cetyl pyridinium bromide or dihydroxyethyl benzyldodecyl ammonium chloride.

The compositions of embodiments of this invention may further be prepared in the form of dusting and scattering preparations using solid vehicles including talcum, kaolin, bentonite, calcium carbonate or phosphate, coal, cork meal, wood meal or other materials of vegetable origin. It is very advantageous to manufacture the preparations in the form of granulates. With the different forms in which the preparations are used, conventional additives that improve the distribution, adhesion, stability towards rain or penetration, e.g. fatty acids, resins, glue, casein or alginates may also be used. Other suitable carriers include, for example, mineral earths, for example, tonsil, silica gel, talc, kaolin, attaclay, limestone and silica acid, and vegetable products, for example, meals.

The compositions of embodiments of this invention may also be admixed with a wetting agent, with or without an inert diluent, to form a wettable powder which is soluble or dispersible in water, or may be mixed with the inert diluent to form a solid or powdery product. Inert diluents with which the active ingredient may be incorporated include solid inert media comprising powdered or divided solid materials, for example, clays, sands, talc, mica, peat, fertilizers and the like, such products either comprising dust or larger particle size materials, e.g., granules.

The wetting agents used may comprise anionic compounds, e.g., soaps, fatty sulphate esters, e.g., dodecyl sodium sulphate, octadecyl sodium sulfate and cetyl sodium sulphate, fatty aromatic sulphonates, e.g., alkyl benzene sulphonates or butyl naphthalene sulphonate, more complex fatty sulphonates, e.g., the amide condensation product of oleic acid and N-methyl taurine or the sodium sulphonate of dioctyl succinate.

The wetting agents may also comprise non-ionic wetting agents, e.g., condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide. The wetting agents may also comprise cationic agents, e.g., octyl trimethyl ammonim bromide and the like. Other suitable surface-active agents include, for example, calcium lignin sulphonate, polyoxyethylenealkyl phenyl ethers, naphthalene sulphonic acids and salts thereof, phenol sulphonic acids and salts thereof, formaldehyde condensates, fatty alcohol sulphates and also substituted benzene sulphonic acids and salts thereof.

The phototoxic naturally-occurring thiophenes, acetylenes or synthetic, structurally-related derivatives, analogues or acetylenic compounds may be provided in the form of a microincapsulated agent, in a manner well known to those skilled in the art. In this way the stability of the naturally-occurring thiophenes, acetylenes or synthetic, structurally-related derivatives, analogues or acetylenic compounds prior to use may be extended.

Suitable formulations, in the forms of stable emulsions are as follows:

| COMPONENT | PREFERRED AMOUNT | USEFUL AMOUNT |
|---|---|---|
| α-Terthienyl | about 5% by weight | about 2-10% by weight |
| ATLOX 3403F | about 4.1% by weight | about 2-10% by weight |
| ATLOX 3403F | about 3.4% by weight | about 2-10% by weight |
| Suitable Solvent | about 87.5% by weight of xylene | balance |

(ATLOX is the trade mark of Atkemix Inc., Brantford, Ontario, Canada, for a series of emulsifers developed for use with agricultural products)

Suitable formulations in the forms, of synergistic compositions are as follows:

| COMPONENT | PREFERRED AMOUNT | USEFUL AMOUNT |
|---|---|---|
| α-Terthienyl | about 5% by weight | about 2-10% by weight |
| piperonyl butoxide | about 5% by weight | about 2-10% by weight |
| ATLOX 3403F | about 4.1% by weight | about 2-10% by weight |
| ATLOX 3404F | about 3.4% by weight | about 2-10% by weight |
| Suitable Solvent | about 82.5% by weight of xylene | balance |

In the use of the compositions of embodiments of this invention as insect control agents, the rate of application may comprise, for example, about 0.01-2 lbs/acre, e.g., about 1.5 lbs/acre.

The total proportion of the phototoxic, naturally-occurring thiophenes, acetylenes, or synthetic, structurally-related derivatives, analogues or acetylenic compounds in the various compositions of embodiments of this invention may vary within wide limits. For example, the compositions may contain approximately 10-80% by weight of phototoxic, naturally-occurring thiophenes, acetylenes or synthetic, structurally-related derivatives, analogues or acetylenic compounds, approximately 90-20% by weight of liquid or solid carrier, and also, if desired, up to about 20% by weight of the carrier of one or more surface-active agents. The rate of dilution of the phototoxic, naturally-occurring thiophenes, acetylenes or synthetic, structurally-related derivatives, analogues or acetylenic compounds in an aqueous spray is not critical and may, for example, be about 1-10 kg/ha phototoxic, naturally-occurring thiophenes, acetylenes or synthetic, structurally-related derivatives, analogues or acetylenic compounds in 300 liters/ha water and about 0.1% surface-active agent, e.g., those mentioned above as wetting agents.

The compositions of embodiments of this invention may be applied in the usual manner, for example, with water as carrier lb/acre. It is also possible to apply the active compounds by the so-called "low volume" and "ultra-low volume" methods and it is also possible to apply them in the form of so-called microgranules.

The following examples illustrate the preparation of some of the compounds of aspects of the invention, so of which have been tested for phototoxic pesticidal activity.

EXAMPLE A

General Experimental

Melting points were determined on a Hoover Unimelt apparatus and are uncorrected. $^1$H N.M.R. and $^{13}$C N.M.R. spectra were done on a Varian XL-300 NMR spectrometer using deuterochloroform as solvent and tetramethylsilane as the internal standard. If other solvents were used, they will be specified. U.V. spectra were obtained on a Hewlett Packard 8451A diode array spectrophotometer. IR spectra were recorded on a Perkin Elmer 783 Infrared spectrometer as a KBr pellet unless otherwise indicated. Mass Spectra were taken on a VG Analytical 7070E mass spectrometer equipped with a Dani 3800 Gas Chromatograph for GC-MS. The HPLC was done using a Varian 5500 HPLC with a U.V. detector. The type of column will be specified for each compound purified in this manner.

Thin layer chromatography was performed on either Baker-Flex pre-coated silica gel 1B2-F plates or Baker pre-coated glass plates. The reverse phase plates used were Whatman KC18f. The silica gel for liquid chromatography was purchased from Terrochem Laboratories, flash chromatography type with 20-435 micron particle size.

All solvents were distilled before use and solvents used for the Grignard reaction were anhydrous. Tetrahydrofuran was distilled over sodium and benzophenone, and 1,2-dimethoxyethane was distilled from sodium onto molecular sieves. Mallinckrodt anhydrous diethyl ether was used undistilled. The petroleum ether used was of the boiling range 35° C.–65° C.

The dichloro-[1,3-bis(diphenylphosphinopropane)]-nickel catalyst for the Grignard-Wurtz coupling reaction was prepared via a known method from the literature (see G. R. Van Hecke & Dew Horrocks, Jr. "Inorg. Chem", 5 1968 (1866)).

EXAMPLE B

General Procedure for the Grignard-Wurtz Coupling Reaction

Magnesium turnings (2.2 eq) and anhydrous diethyl ether were placed in a three-necked flask, equipped with a reflux condenser, an inlet tube for passing a current of nitrogen and an additional funnel. The reaction was started by adding a small crystal of iodine while a solution of 2-bromothiophene (2 eq) in anhydrous diethyl ether was slowly added dropwise under nitrogen with magnetic stirring. The reaction was stirred for 45 minutes after the addition of the 2-bromothiophene was complete.

The solution of 2-thienylmagnesium bromide was poured into a separatory funnel and added dropwise with stirring under nitrogen to the appropriate brominated substrate(1 eq) in anhydrous diethyl ether. Dichloro-[1,3-bis(diphenylphosphinopropane)]-nickel (trace) was added as catalyst. The reaction was stirred for 24 h at room temperature and then worked up with 3N HCl. The diethyl ether layer was separated and washed with water. It was then dried over magnesium sulphate and the solvent removed under reduced pressure. Crystallization, liquid chromatography or HPLC were used to purify the coupled product.

EXAMPLE I

Preparation of 2,6-(Di-2-thienyl)-pyridine

2-Bromothiophene (5 ml, 1.051 m) in anhydrous ether (25 ml) was added to magnesium turnings (1.2 g, 0.05 m) and a trace of iodine in diethyl ether (40 ml). It was stirred for one hour and then added to 2,6-dibromopyridine (4.5 g, 0.019 m) and nickel catalyst in diethyl ether (30 ml). The reaction was stirred for 24 h at room temperature. After workup, dark brown crystals (4 g, 86% crude yield) were isolated.

The crystals (2.15 g) were chromatographed on flash silica with 4 lbs of pressure. Petroleum ether was the eluant. A pale yellow crystalline solid (1.89 g, 76% yield) was separated; m.p., 79°–80° C. (lit m.p. 78°–79° C.); m/z 243 (M+); λmax 280 nm and 325 nm; (Found: C,64.36; H,3.81; S,26.02; N,5.78. $C_{13}H_9NS_2$ requires C,64.2; H,3.7; S,26.3; N,5.80); H NMR (Acetone d₆) δ7.78 (dd, J=<1, 4 Hz, 2H), δ7.16 (dd, J=4,6 Hz, 2H), δ7.57 (dd, J=<1, 6 Hz 2H), δ7.71 (dd, J=7, 1 Hz, 2H), δ7.83 (dd, J=7 Hz, 1H).

EXAMPLE II

Preparation of 1,3-(Di-2-thienyl)-benzene

The Grignard was prepared by adding 2-bromothiophene (8.15 g, 0.05 m) in diethyl ether (10 ml) to magnesium turnings (1.22 g, 0.05 m) and iodine (trace) in diethyl ether (15 ml). After 1 h, the Grignard was slowly added to 1,3-dibromobenzene (5.0 g, 0.021 m) and catalyst in diethyl ether (20 ml). Workup after 24 h afforded a residue which crystallized from hot hexanes yielding a green solid (540 mg, 10% crude yield). The green solid (190 mg) was purified by column chromatography using petroleum ether as the eluant. A light green crystalline solid (136 mg, 7.6% yield) was separated; m.p. 83°–84° C., m/z 242 (M+); Found: C, 69.22; H, 4.04; S, 26.09; $C_{14}H_{10}S_2$ requires: C,69.4; H, 4.1; S, 26.4 H NMR (CDCl₃) δ7.35 (dd, J=<1, 3 Hz, 2H), δ7.085 (dd, J=5,3 Hz, 2H), δ7.29 (dd, J=<1, 5 Hz, 2H), δ7.81 (t, J=<1 Hz, 1H), δ7.38 (dd, J=8 Hz, 1H), δ7.51 (ddd, J=<1,2, 8 Hz, 2H).

EXAMPLE III

Preparation of 1,4-(Di-2-thienyl)-benzene

2-Bromothiophene (22.5 g, 0.15 m) in diethyl ether (150 ml) was added to magnesium turnings (4 g, 0.15 m) and iodine (trace) in diethyl ether (25 ml). The Grignard was added to 1,4-dibromobenzene (13 g, 0.55 m) and nickel catalyst in diethyl ether (25 ml). The reaction mixture was refluxed under nitrogen for 10 h, and at room temperature for another 36 h. The reaction was worked up in the usual fashion. The crude residue was dissolved in hot hexanes (75 ml) and filtered to remove insoluble material. After evaporation of the hexane to 40 ml and cooling, orange plate-like crystals (1.0 g) separated. An orange solid (4.9 g) was also obtained by filtering the water layer and washing the water with benzene (44% crude yield). 1,4-Di-2-thienylbenzene (0.66 g) was further purified by column chromatography using 1.5% diethyl ether/petroleum ether as eluant. Bright yellow crystals (153 mg) were isolated. The remainder of the product was recrystallized from hot benzene affording yellow-orange crystals (1.9 g, 15% yield); m.p. 207°–208° C., (lit. m.p. 208° C.); m/z 242 (M+) (Found: C, 69.29; H, 4.03; S, 26.33). Required for $C_{14}H_{10}S_2$; C, 69.42; H, 4.13; S, 26.45. H NMR (CDCl₃) δ7.28 (dd, J=3.6, 1.2 Hz, 2H), δ7.04 (dd, J=3.6 Hz, 5.4 Hz, 2H), δ7.23 (dd, J=5.4, 1.2 Hz, 2H), δ7.56 (s, 4H).

EXAMPLE IV

Preparation of 1-(2-Thienyl)-Naphthalene

2-Bromothiophene(1.45 ml, 0.015 m) in diethyl ether (20 ml) was added slowly to magnesium turnings (0.48 g, 0.02 m) and iodine (trace) in diethyl ether (10 ml). It was stirred for 30 min before being added to 1-bromonaphthalene (2.07 g, 0.01 m) and catalyst in diethyl ether (25 ml). The reaction was worked up the usual way yielding a brown oil (2.49 g). The brown oil was purified by column chromatography. Flash silica (104 g) eluted with petroleum ether (600 ml) and increased to 5% diethyl diethyl ether/petroleum ether separated a clear pale green oil (1.50 g, 71% yield); m/z 210 (M+); (Found: C, 80.26; H, 4.91; S, 15.10. $C_{14}H_{10}S$ requires: C, 80.00; H, 4.76; S, 15.24); H NMR (CDCl₃), δ7.17 (dd, J=3.2, 5.6 Hz 1H), δ7.23 (dd, J=<1, 3.2 Hz, 1H), δ7.41 (dd, J=<1, 5.6 Hz, 1H), δ7.45 (d, J=4.8 Hz, 1H), δ7.47 (d, J=4.8 Hz, 1H) δ7.48 (d, J=8 Hz, 1H), δ7.55 (dd, J=<1, 8 Hz, 1H), δ7.83 (d, J=8 Hz, 1H), δ7.88 (dd J=3.2, 4.8 Hz, 1H), δ8.20 (dd, J=5.6, 4.8 Hz, 1H).

EXAMPLE V

Preparation of 2-(2-Thienyl)-Naphthalene

The 2-(2-thienyl)-naphthalene was prepared in the same manner as for the 1-thienyl-naphthalene derivative, with the Grignard being added to 2-bromonaphthalene (2.07 g, 0.01 m). After workup, a brown solid (2.39 g) was isolated. Column chromatography yielded 2-bromonaphthalene (630 mg) and a white crystalline solid (1.13 g, 73% yield based on recovered starting material); m.p. 103°–104° C.; m/z 210 (M+); (Found: C, 79.75; H, 4,80; S, 15.09. $C_{14}H_{10}S$ requires C, 80.0; H, 4.76; S, 15.24); H NMR (CDCl₃); δ7.17 (dd, J=5.6, 3.5 Hz, 1H), δ7.30 (dd, J=<1, 5.6 Hz, 1H), δ7.42 (dd, J=<1, 5 Hz 1H), δ7.45 (dd, J=<1, 7 Hz, 1H), δ7.46 (dd, J=1, 4.0 Hz, 1H), δ7.73 (dd, J=1, 8.0 Hz, 1H), δ7.79 (dd, J=1, 8 Hz, 1H), δ7.81 (s, 1H), δ7.83 (s, 1H), δ5.803 (d, <1, Hz, 1H).

DERIVATIVES OF 2,2':5',2''-Terthienyl

α-Terthienyl (a known compound) was used as starting material for the following derivatives. α-Terthienyl has the following NMR characteristics; H NMR (CDCl₃), δ7.20 (dd, J=5.2 Hz, 2H), δ7.01 (dd, J=3.6 Hz, 2H), δ7.16 (dd, J=<1 Hz, 2H), δ7.06 (s, 2H).

EXAMPLE VI

Preparation of 5-methyl-2,2':5',2''-Terthienyl

α-Terthienyl (1.0 g, 0.004 m) was dissolved in dry tetrahydrofuran (75 ml) and cooled to −78° C. via an acetone/CO₂bath. All glassware was oven dried and the butyl lithium titrated before use. The reaction was carried out over nitrogen. Butyl lithium (1.92 ml, 2.08M) was added to the cooled solution dropwise over 15 min. The yellow lithium salt precipitated out of solution. The mixture was left to stir for 0.5 h at which time methyl iodide (0.5 ml, 0.008 m) was slowly added. The reaction was stirred for 2 h at −78° C. and then allowed to warm up to room temperature. At −30° C., the lithium salt rapidly disappeared leaving a clear orange solution. After stirring at room temperature for 24 h, the reaction was worked up with 3N HCl. Methylene chloride (50 ml) was added and the organic layer was separated and washed with water. It was then dried over magnesium sulphate and removed by rotary evaporation, yielding a brown-green solid (1.12 g).

The crude solid was chromatographed with silica (52 g) using petroleum ether as the eluant. A bright yellow solid (0.93 g) was isolated which was found to be a mixture of α-terthienyl and the mono- and dimethylated products. The products were separated by HPLC using an MCH-5NCAP column (analytical) purchased from Varian and eluting with 5% H₂O/95% CH₃OH. The product ratio of the reaction mixture using integrated peak areas was α-terthienyl-7%, 5-methyl-2,2':5'2"-terthienyl-69%, and 5,5"-dimethyl-2,2':5',2"-terthienyl-23%. Preparative HPLC using 2% $H_2O$/98% $CH_3OH$ as eluant was performed using a Serva ODS 100 polyol column (22 mm × 500 mm, with 5 micron particle size). m.p. 94.5°–95.5° C. (lit. 93°–94.5° C., m/z 262 (M+); H NMR ($CDCl_3$), δ2.46 (d, J=<1 Hz, 3H), δ6.65 (m, J=<1, 3.2 Hz, 1H), δ6.94 (d, J=3.2 Hz, 1H), δ6.97 (d, J=3.2 Hz, 1H), δ7.02 (d, J=3.2 Hz, 1H), δ7.13 (dd, J=1, 3.2 Hz, 1H), δ6.70 (dd, J=3.2, 5.2 Hz, 1 Hz), δ7.19 (dd, J=<1, 5.2 Hz, 1H).

EXAMPLE VII

Preparation of 5,5"-Dimethyl-2,2':5',2"-Terthienyl

The procedure for synthesizing the dimethylated derivative was similar to that of 5-methyl-α-terthienyl so only the modifications will be mentioned here. The butyl lithium (3.96 ml, 2.02M) was slowly added to the solution of α-terthienyl (1.0 g, 0.004 m) in tetrahydrofuran (75 ml) which was kept between −50° and −40° C. in an acetone/$CO_2$ bath. The mixture was stirred at this temperature for 45 min at which time methyl iodide (0.75 ml, 0.012 m) was slowly added. It was stirred for 20 min and then allowed to warm up to room temperature. At 4° C., most of the lithium salt had disappeared leaving an almost clear orange solution. After workup, a green solid was isolated (1.23 g).

Liquid chromatography yielded a bright yellow solid (0.90 g) which showed by reverse phase TLC (90% ethanol/10% water), a mixture of mono and dimethylated α-terthienyl. HPLC using the MCH-5NCAP reverse phase analytical column by Varian and eluting with 5% $H_2O$/95% $CH_3OH$ showed the mixture to be 5-Methyl-2,2':5',2"-terthienyl-16%, and 5,5"-dimethyl-2,2':5',2"-terthienyl-82%. Preparative HPLC using the Serva ODS 100 polyol column (22 mm × 500 mm, 5 micron particle size) and eluting with 2% $H_2O$/98% $CH_3OH$ yielded a yellow-orange solid. m.p. 96°–97° C., (lit. 98°–99° C.), m/z 276 (M+), (Found: C,60.34; H,4.36; S,35.04. $C_{14}H_{12}S_3$ requires: C,60.87; H,4.34; S,34.78.); H NMR ($CDCl_3$) δ2.46 (s, 6H), δ6.64 (m, J=<1, 4 Hz, 2H), δ6.92 (d, J=4 Hz, 2H), δ=6.94 (s, 2H).

EXAMPLE VIII

Preparation of 5-Cyano-2,2':5',2"-Terthienyl

To a solution of α-terthienyl(2.46 g, 0.010 m) in methylene chloride (20 ml), was added chlorosulfonyl isocyanate (1.75 ml) in methylene chloride (15 ml). A yellow solid separated almost at once. The reaction mixture was stirred for 2 h and left overnight. Dimethyl formamide (5.0 ml) was added to the ice-cold reaction mixture dropwise. Addition of water (40 ml) precipitated a yellow solid insoluble in methylene chloride. The latter was removed in vacuo and the yellowish green solid was collected in a Buchner funnel and washed with water. Yield: 2 g; m.p. 122°–125° C. Recrystallization from the minimum amount of boiling ethanol-benzene(1:1) afforded 1.6 g of product(58.6% crude yield).

The recrystallized material (500 mg) was chromatographed on flash silica (110 g), eluted with 3% ethyl acetate/hexane and gradually increased to 15% ethyl acetate. A bright yellow solid (234 mg, 27.4% yield) was isolated. m.p. 101°–105° C., m/z 273 (M+); H NMR (Acetone-$d_6$) δ7.81 (d, J=3.5 Hz, 1H), δ7.30 (d, J=3.5 Hz, 1H), δ7.42 (d, J=3.7 Hz, 1H), δ7.46 (d, J=3.7 Hz, 1H), δ7.38 (dd, J=<1, 3.5 Hz, 1H), δ7.12 (dd, J=3.5, 5.5 Hz, 1H), δ7.50 (dd, J=1, 5.5 Hz, 1H). (Found: C, 57.45, H, 2.87; S, 34.49, N, 4.89; $C_{13}H_7S_3N$ requires C, 57.10; H, 2.56; S, 35.10; N, 5.13).

EXAMPLE IX

Preparation of 5,5"-Dicyano-2,2':5',2"-Terthienyl

α-Terthienyl (2.46 g, 0.01 m) was treated with two equivalents of chlorosulfonyl isocyanate (0.02 m) in methylene chloride as described in the preparation of 5-cyano-2,2':5',2"-terthienyl. Work-up as in that procedure gave crude product (2.4 g), m.p. 165°–170° C., contracting around 140° C. m/z 298(m+);

H NMR (DMSO-$d_6$), δ7.98 (d, J=4 Hz, 2H), δ7.62 (s, 2H), δ7.58 (d, J=4 Hz, 2H).

EXAMPLE X

Preparation of 5-Nitro- and 5,5"-Dinitro-2,2':5'2"-Terthienyl

To a solution of α-terthienyl (1.24 g, 0.005 m) in methylene chloride (10 ml) and acetic anhydride (10 ml) at 5° C. was added with stirring, 3.5 ml of a solution of fuming nitric acid (3.0 ml) in glacial acetic acid (30 ml). The reaction mixture which became slightly warm was stirred at room temperature for 6 h. It was then poured into water (60 ml) and stirred for 30 min to hydrolyse the acetic anhydride. The reddish brown precipitate obtained after removing methylene chloride in vacuo was collected in a Buchner funnel and washed with water. Yield; 1.3 g; m.p. 128°–130° C., shrinking somewhat at 124° C. TLC (20% ethyl acetate/hexane) showed the product to be a mixture of mono and dinitro-α-terthienyl.

The mixture (300 mg) was separated by liquid chromatography using flash silica (76 g) and eluting with hexane gradually increasing to 5% ethyl acetate/hexane. A red-brown solid (110 mg, 36% yield) was isolated and was determined to be the mono-nitro derivative. m.p. 139°–141° C.; m/z 293 (M+); Mono-nitro: H NMR ($CDCl_3$), δ7.83 (d, J=4 Hz, 1H), δ7.05 (d, J=4 Hz, 1H), δ7.12 (d, J=3 Hz, 1H), δ7.26 (d, J=3 Hz, 1H), δ7.22 (dd, J=<1, 3 Hz, 1H), δ7.04 (dd, J=3, 5.2 Hz, 1H), δ7.28 (dd, J=<1, 5.2 Hz, 1H).

EXAMPLE XI

Preparation of 5-Iodo-2,2':5',2"-Terthienyl

α-Terthienyl (2.06 g, 0.0084 m) was dissolved in benzene (50 ml), HgO(1.5 g, 0.007 m) and $I_2$(2.18 g, 0.018 m) were added. The mixture was left to stir for 17 h. At this time TLC (petroleum ether eluant) showed the presence of a large amount of starting material, so HgO (0.5 g, 0.0023 m) and $I_2$(1 g, 0.004 m) were again added. The mixture was stirred for another 15 h. The $HgI_2$(4.75 g) was filtered off and the solution washed with sodium thiosulfate (300 ml, 10%). The benzene was then dried over magnesium sulfate and removed under reduced pressure yielding a brown solid (1.2 g).

The product was dissolved in hexane, and the insoluble material filtered off (200 mg). It was mostly the diiodinated derivative. m.p. 184°–185° C. On cooling, 5-iodo-α-terthienyl(594 mg, 19% yield) crystallized from the hexane. m.p. 138°–139° C., m/z 374 (M+); H NMR (DMSO-$d_6$), δ7.10 (d, J=3.6 Hz, 1H), δ7.36 (d, J=3.6 Hz, 1H), δ7.28 (m, 2H), δ7.38 (dd, J=3.6, 1 Hz, 1H), δ7.14 (dd, J=3.6, 5.4 Hz, 1H), δ7.56 (dd, J=5.4, 1 Hz, 1H).

EXAMPLE XII

Preparation of 5,5''-Diiodo-2,2':5'2-Terthienyl

α-Terthienyl(2.48 g, 0.01 m), HgO(3.0 g, 0.0138 m) and I$_2$(4.36 g, 0.017 m) were added to CHCl$_3$ (75 ml) and the reaction stirred for 18 h. TLC showed the presence of α-terthienyl so further HgO(1 g, 0.0046 m) and I$_2$ (2 g, 0.0079 m) were added and the reaction stirred for 24 h. Filteration of HgI$_2$ and removal of benzene on a rotary evaporator afforded a pale brown solid. Hot benzene was added to the solid and the undissolved material, the diiodinated product, was filtered off (1.2 g, 24% yield). m.p. 188°–190° C., m/z 500 (M+); H NMR (CDCl$_3$), δ6.86 (d, J=3.6 Hz, 2H), δ7.18 (d, J=3.6 Hz, 2H), δ7.04 (s, 2H).

EXAMPLE XIII

Preparation of 5-Bromo- and 5,5''-Dibromo-2,2':5',2''-Terthienyl

α-Terthienyl (2.46 g, 0.01 m) and N-bromosuccinimide (NBS) (1.96 g, 0.11 m) were dissolved in CCl$_4$ (50 ml) and refluxed for 10 h. The succinimide floated on top of the solution and the solution turned from yellow to green. The imide was filtered off and the filtrate removed under reduced pressure yielding a green solid (4.2 g). By TLC the product was a mixture of monobrominated and dibrominated α-terthienyl with very little unreacted starting material.

Liquid chromatography yielded only partial separation, so the yield was determined by HPLC using a Beckman ODS DP5M (6 mm ID, 25 cm) reverse phase column and eluting with acetonitrile. The reaction mixture was determined to be 5-bromo-α-terthienyl-57% and 5,5''-dibromo-α-terthienyl-26%. For the monobrominated derivative: m.p. 136°–137.5° C., m/z 326,328 (M+), (Found C, 44.17; H, 2.10; S, 29.45; Br, 24.59. C$_{12}$H$_7$S$_3$Br requires C,44.03; H, 2.14; S, 29.36, Br, 24.5) H NMR (CDCl$_3$), δ6.89 (d, J=3.6 Hz, 1H), δ6.95 (d, J= 3.6 Hz, 1H), δ6.99 (d, J=3.6 Hz, 1H), δ7.05 (d, J=3.6 Hz, 1H), δ7.15 (dd, J=3.6, 1 Hz, 1H), δ7.00 (dd, J=5.4, 3.6 Hz, 1H), δ7.21 (dd, J=<1, 5.4 Hz; 1H). For the dibrominated derivative: m.p. 156°–157° C. (lit. ref. 160°–161° C.), m/z 404,406,408 (M+); H NMR (CDCl$_3$) δ6.89 (d, J=3.6 Hz, 2H), δ6.96 (d, J=3.6 Hz, 2H), δ6.97 (s, 2H).

EXAMPLE XIV

Preparation of 5-Formyl-2,2':5',2''-Terthienyl

N-Methylformanilide (3.4 ml) and phosphorous oxychloride (4.0 g, 2.25 ml) were mixed and left to stand for 1 h to allow the reagent to form. A solution of α-terthienyl (6.2 g, 0.05 ml) in methylene chloride (25 ml) was added with stirring. There was no appreciable rise in temperature. The reaction mixture was stirred for 20 h before pouring it into HCl (75 ml) and stirring for 1 hr to remove dimethylaniline as the hydrochloride. The methylene chloride extract was freed of solvent in vacuo leaving an orange solid as residue. It was recrystallized from hot benzene (50 ml) yielding orange crystals (2.4 g) m.p. 135°–136° C. Evaporation of the mother liquor gave orange crystals (3.4 g) which by TLC were a mixture of α-terthienyl and the 5-formyl-α-terthienyl. m/z 276 (M+); H NMR (Acetone-d$_6$), δ9.92 (s, 1H), δ7.93 (d, J=3.6 Hz, 1H), δ7.30 (d, J=3.6 Hz, 1H), δ7.49 (d, J=3.6 Hz, 1H), δ7.12 (dd, J=4.2, 5.4 Hz, 1H), δ7.50 (dd, J=<1, 5.4 Hz, 1H). (Found: C, 56.03; H, 2.87; S, 34.7, C$_{13}$H$_8$S$_3$O requires C, 56.50; H, 2.89; S, 34.8.).

EXAMPLE XV

Preparation of 2-[2,2':5,2''-Terthienyl]-ethanol

α-Terthienyl lithium was prepared by adding, under nitrogen, butyllithium (2.0 ml, 2.0M) via a syringe and septum to a stirred solution of α-terthienyl in anhydrous tetrahydrofuran (50 ml) cooled to −40° C. in a dry ice acetone bath. After 1 h of stirring at −20° C., excess ethylene oxide was bubbled through the yellow suspension of the lithium salt for 10 min. The reaction mixture was allowed to come to room temperature, stirred for 20 h and acidified by addition of 3N HCl. Tetrahydrofuran was removed under vacuum and the residual oil was taken up in diethyl ether. Evaporation of the dried diethyl ether solution under vacuum left a green solid. Yield; 1.1 g. Recrystallization from ethanol and then hexane gave green crystals (0.50 g), m.p. 85°–87° C. A fraction which remained undissolved in ethanol m.p. 116°–118° C. was probably the diol; H NMR (CDCl$_3$), δ3.87 (t, J=6 Hz, 2H), δ3.02 (t, J=6 Hz, 2H), δ6.77 (dt, J=<1, 3.6 Hz, 1H), δ7.05 (d, J=3.6 Hz, 1H), δ6.99 (d, J=2.4 Hz, 1H), δ7.00 (d, J=2.4, 1H), δ7.14 (dd, J=<1, 5.2 Hz, 1H), δ7.00 (dd, J=3.4, 5.2 Hz, 1H), δ7.20 (dd, J=<1, 3.4 Hz, 1H).

EXAMPLE XVI

Preparation of 2-[2,2':5'-Terthienyl]-3-propanol

This alcohol was prepared in the same manner as the lower homologue by adding trimethylene oxide to the lithium salt of α-terthienyl. The crude product recrystallized from ethanol was a green solid, m.p. 85°–90° C. By TLC the product was a mixture of the propanol derivative and α-terthienyl.

EXAMPLE XVII

Preparation of 5-Carboxy-2,2':5',2''-Terthienyl

The mother liquor from the recrystallization of the 2-cyanoα-terthienyl was evaporated to dryness in vacuo and the residue was heated in ethanol-water (25 ml, 1:1) containing a pellet of sodium hydroxide until no more ammonia came off. The reaction mixture was then acidified with 3N HCl and the acid was collected on a Buchner funnel. Yield 1.0 g.

EXAMPLE XVIII

Preparation of 5-[2,2':5',2''-Terthienyl]Acrylic Acid

A mixture of 5-formyl-2,2':5',2''-terthienyl (2.7 g, 0.01 m), malonic acid (2.0 g) and piperidine (0.1 ml) in pyridine (20 ml) was heated until there was no evolution of CO$_2$ through a bubble counter on top of the reflux condenser. This took 2 h. The cold reaction mixture was poured into 2N HCl (75 ml). The orange precipitate was collected on a Buchner funnel and washed copiously with water. It was digested with dilute sodium hydroxide in ethanol (50 ml, 25%). Insoluble material was collected on a filter and was treated as described later. Acidification of the yellow filtrate precipitated a red solid (100 mg). m.p. 190°–191° C. with decomposition, probably evolution of CO$_2$. Both the yellow precipitate and the red precipitate gave the same MS ion m/z 318 (M+). They are probably the cis and trans isomers.

The insoluble product was digested with hot dilute HCl and filtered off. It amounted to 2.0 g and melted at 230° C. Recrystallization from glacial acetic acid (200 ml) resulted in a yellow product melting at 220°–225° C. with decomposition. The yield was 1.5 g. m/z 318 (M+).

EXAMPLE XIX

Preparation of 3:4'-Dimethyl-2,2':5',2''-Terthienyl

To a benzene (30 ml) solution of ethyltriphenylphosphonium bromide (2.08 g, 5.6 mm), sodium amide (1.1 g, 18 mm) was added in one portion. The reaction mixture was stirred at room temperature under nitrogen. After 24 h, the mixture was filtered and cooled in an ice-bath under nitrogen. A solution of 2-thiophenecarbodithioic acid methyl ester (0.098 g, 5.6 mm) in benzene (10 ml) was added in one portion. After 15 min., the mixture was allowed to stay at room temperature for 3 h. The solvent was then evaporated under vacuum yielding a dark oil which, after liquid chromatography, gave a yellow solid [(m.p. 153°–155° C.), m/z 416 (M+)]. The yellow product was pyrolized for 30 min. at 180°–200° C. A dark brown oil solidified upon cooling. It was chromatographed over silica with petroleum ether as the elvant. A white solid (0.03 g) was separated in 18.5% yield from the ester; m.p. 123°–125° C., m/z 276 (M+).

EXAMPLE XX

Preparation of 3'4'-Diethyl-2'2:5',5-Terthienyl

The preparation of the 3',4'diethyl derivative was similar to that of the 3',4'dimethyl derivative except that propyl-triphenylphosphonium bromide (2.15 g, 5.6 mm) was used. The product was isolated as a yellowish oil (0.02 g) in 7% yield from the ester. m/z 304 (M+).

The phototoxicity of some of the above prepared naturally-occurring thiophenes, acetylenes and synthetic, structurally-related derivatives, analogues and acetylenic compounds to mosquito larvae was carried out in the following manner:

1. Insect rearing and toxicity tests.

*Aedes atropalpus* larvae from a stock maintained in the laboratory were used (see B. J. R. Philogène, J. T. Arnason, C. W. Berg, F. Duval, D. Champagne, R. C. Taylor, L. C. Leitch, and P. Morand. 1985. J. Econ. Ent. 78: 121–126). Toxicity tests were performed as described in T. Arnason, T. Swain, C. K. Wat, E. A. Graham, S. Partington, G. H. N. Towers, and J. Lam. 1981. Biochem. Syst. Ecol. 9: 63–68.

Compounds 31 to 34 were extracted from plant sources. Compound 33 was isolated from roots of *Chrysanthemum leucanthemum* L., compound 34 (carlina oxide) from *Carlina acaulis* (caulescens) L., compound 32, (pontica epoxide) from *Artemisia pontica* L., and compound 31 from *Santolina chamaecyparissus* L. (see Bohlmann, F., W. v. Kap-Herr, L. Fanghanel, and C. Arndt. 1965. Che. Ber. 98, 1411–1415. Semmler, F. W. 1889. Chemiker-Zeitung 13, 1158. Bohlmann, F., C. Arndt, and H. Bornowski. 1960. Chem. Ber. 93, 1937–1944. Bohlmann, F., and C. Arndt. 1966. Chem. Ber. 99, 135–137).

A series of analogues two series of derivatives of α-terthienyl compounds were investigated: a methyl-substituted series (compounds 17, 6), an iodosubstituted series (compounds 63, 35) and a series in which the middle ring was substituted (compounds 50, 15). Only the 5-methyl substituted derivative (compound 6) increased photoxicity (See Table 1), while the 3',4'-dimethyl derivative was an order of magnitude less toxic than compound 34. In the iodo-series, activity declines rapidly in the order of increasing iodination: compound 72, compound 43 and compound 35. In the third series, the substitution of the middle ring with a benzene ring (compound 50) slightly reduces activity while pyridine substitution (compound 15) reduces the phototoxic effect by an order of magnitude. In this series, the chromophore is altered and in the case of compound 50 there is no absorption in the photosensitizing region (300–440 nm). This latter compound is the only one in the series that shows no significant enhancement under irradiation as compared to dark conditions and its activity can be attributed to non-photosensitizing effects. This activity is much higher than the non-photosensitizing toxicity of α-terthienyl (LD$_{50}$=0.74 ppm).

In the second series compound, 33 is the most active. Replacement of the triacetylene portion of the molecule with a thienyl-acetylene (compound 31) reduces the activity by an order of magnitude. Similarly replacement of the furan of compound 33 with an epoxide in compound 34 produces an even greater reduction of activity. Compound 32 with both a phenyl and furan ring showed the least activity.

The results are summarized below in Table II.

TABLE II

Acute 24 hr phototoxicity of analogues to *Aedes atropalpus larvae.*

| Compound # (as previously defined) | LC$_{50}$ (ppm) | LC$_{90}$ (ppm) | r |
|---|---|---|---|
| 72 | 0.0275 | 0.0422 | 1.00 |
| 43 | 30.7 | 9330 | 0.989 |
| 35 | <1 | <1 | — |
| 50 | 0.060 | 0.320 | 0.820 |
| 15 | 0.261 | 0.680 | 1.00 |
| 17 | 0.0153 | 0.0269 | 0.932 |
| 6 | 0.164 | 0.209 | 0.998 |
| 33 | 0.100 | 0.300 | 0.952 |
| 31 | 0.858 | 1.57 | 0.992 |
| 34 | 1.47 | 8.91 | 0.999 |
| 32 | 3.71 | 6.30 | 1.00 |

Note:
Larvae in 100 ml of water were treated with 4 hr near-UV irradiation from a bank of 4 blacklight blue tubes (4 w/m²) immediately following addition of test compound, then held in the dark for a further 20 hr. No mortality was seen in controls.

We claim:

1. A pesticidal composition comprising a carrier and a biocidal-amount of a phototoxic naturally-occurring thiophene, acetylene or synthetic, structurally-related derivatives, analogue or acetylenic compound selected from the group consisting of (a) compound of the formula

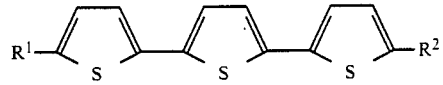

wherein
$R^1=R^2=CO_2H$;
$R^1=CO_2H$; $R^2=H$;
$R^1$=tritium; $R^2=COCH_3$;
$R^1=R^2=COCH_3$;
$R^1=CH_2OH$; $R^2=H$;
$R^1=CHO$; $R^2=H$;
$R^1=R^2=CHO$;
$R^1=R^2=C\equiv N$;
$R^1=NH_2$; $R^2=H$;
$R^1=(CH_2)_2OH$; $R^2=H$;
$R^1=C\equiv N$; $R^2=H$;

$R^1$=CH=CHCO$_2$H(cis), $R^2$=H; and
$R^1$=CH=CHCO$_2$H(trans); $R^2$=H;

(b) compound of the formula

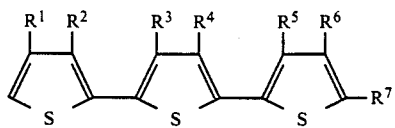

wherein
$R^1$=$R^2$=$R^3$=$R^4$=$R^5$=$R^6$=CH$_3$; $R^7$=H;
$R^1$=$R^2$=$R^5$=$R^6$=$R^7$=H; $R^3$=$R^4$=CH$_3$;
$R^1$=$R^4$=$R^6$=$R^7$=H; $R^2$=$R^3$=$R^5$=CH$_3$; and
$R^1$=$R^2$=$R^5$=$R^6$=$R^7$=H; $R^3$=$R^4$=CH$_3$CH$_2$;
and (c) an α-terthienyl of the formula (where a dot indicates the point of attachment):

wherein

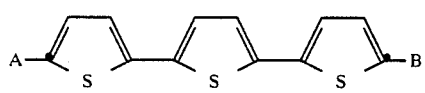, and R = Cl;

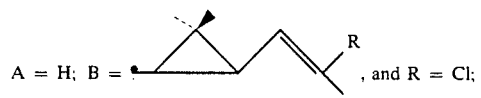, and R = CH$_3$;

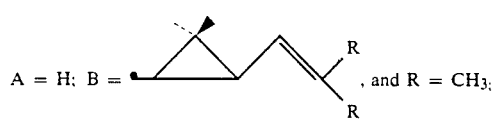, and R = Br;

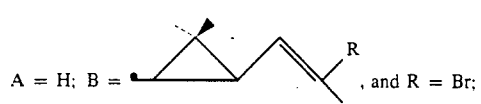, and R = CF$_3$;

, and R' = H;

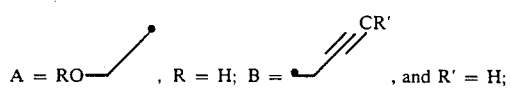, and R' = H;

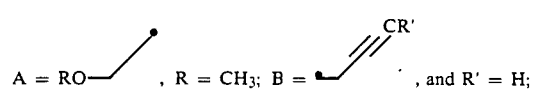, and R' = CH$_3$;

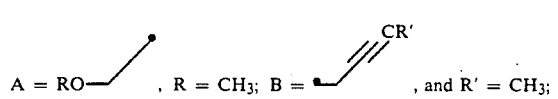, and R' = CH$_3$;

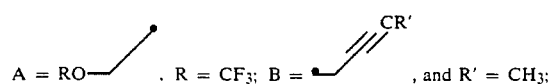, and R = CF$_3$, Cl. or Br;

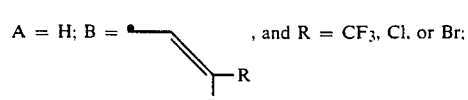, and R = Cl;

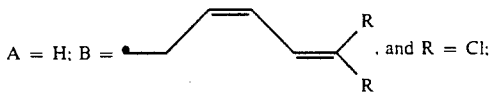, and R = Br;

, and R = CF$_3$;

;

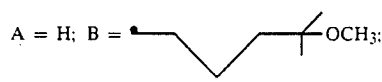;

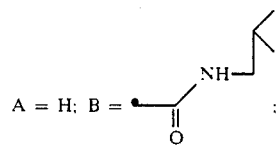;

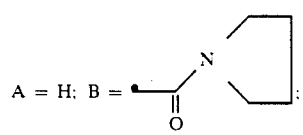; and

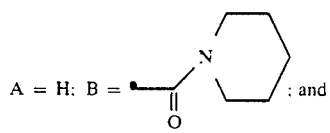

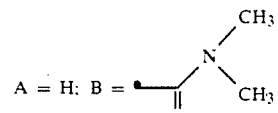

2. A pesticidal composition according to claim 1, wherein said phototoxic compound is selected from Group (a).

3. A pesticidal composition according to claim 1, wherein said phototoxic compound is selected from Group (b).

4. A pesticidal composition according to claim 1, wherein said phototoxic compound is selected from Group (c).

5. A pesticidal composition comprising a carrier and a biocidal-amount of a phototoxic, naturally-occurring compound of the following Formula:

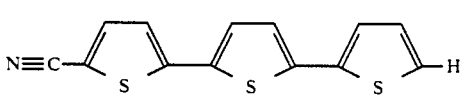

6. A pesticidal composition comprising a carrier and a biocidal-amount of a phototoxic, naturally-occurring compound of the following Formula:

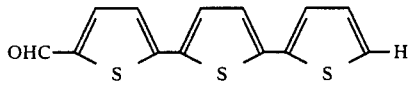

7. A pesticidal composition comprising a carrier and a biocidal-amount of a phototoxic, naturally-occurring compound of the following Formula:

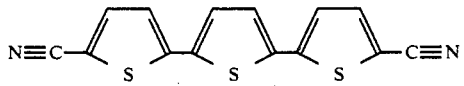

8. The pesticidal composition of claim 5 wherein said composition includes at least one of a solvent, a diluent, a dispersing agent or a wetting agent.

9. The pesticidal composition of claim 6 wherein said composition includes at least one of a solvent, a diluent, a dispersing agent or a wetting agent.

10. The pesticidal composition of claim 7 wherein said composition includes at least one of a solvent, a diluent, a dispersing agent or a wetting agent.

11. The composition of claim 5 which is in the form of a powder, a strewable preparation, granules, solutions, emulsions or suspensions.

12. The composition of claim 6 which is in the form of a powder, a strewable preparation, granules, solutions, emulsions or suspensions.

13. The composition of claim 7 which is in the form of a powder, a strewable preparation, granules, solutions, emulsions or suspensions.

14. The pesticidal composition of claim 5 which is in the form of a solution in an organic solvent.

15. The pesticidal composition of claim 6 which is in the form of a solution in an organic solvent.

16. The pesticidal composition of claim 7 which is in the form of a solution in an organic solvent.

17. The pesticidal composition of claim 5 which is in the form of an aqueous solution containing a non-ionic, or anionic or a cationic emulsifying or dispersing agent.

18. The pesticidal composition of claim 6 which is in the form of an aqueous solution containing a non-ionic, or anionic or a cationic emulsifying or dispersing agent.

19. The pesticidal composition of claim 7 which is in the form of an aqueous solution containing a non-ionic, or anionic or a cationic emulsifying or dispersing agent.

20. The pesticidal composition of claim 5 which is in the form of a dusting powder.

21. The pesticidal composition of claim 20 including a wetting agent therein.

22. The pesticidal composition of claim 6 which is in the form of a dusting powder.

23. The pesticidal composition of claim 22 including a wetting agent therein.

24. The pesticidal composition of claim 7 which is in the form of a dusting powder.

25. The pesticidal composition of claim 24 including a wetting agent therein.

26. The pesticidal composition of claim 5 which is in the form of a microencapsulated material.

27. The pesticidal composition of claim 6 which is in the form of a microencapsulated material.

28. The pesticidal composition of claim 7 which is in the form of a microencapsulated material.

29. The pesticidal composition of claim 5 including an organic solvent and an emulsifier therein.

30. The pesticidal composition of claim 6 including an organic solvent and an emulsifier therein.

31. The pesticidal composition of claim 7 including an organic solvent and an emulsifier therein.

* * * * *